United States Patent [19]
Cleveland

[11] 3,946,062
[45]* Mar. 23, 1976

[54] PREPARATION OF 2-CHLOROCYCLOALKYLTHIO UREA COMPOUNDS

[75] Inventor: James D. Cleveland, Albany, Calif.

[73] Assignee: Chevron Research Company, San Francisco, Calif.

[ * ] Notice: The portion of the term of this patent subsequent to Dec. 24, 1991, has been disclaimed.

[22] Filed: Sept. 27, 1974

[21] Appl. No.: 509,753

Related U.S. Application Data

[63] Continuation-in-part of Ser. No. 250,895, May 8, 1972, Pat. No. 3,857,883.

[52] U.S. Cl. ............ 260/453 R; 71/98; 260/543 H; 260/553 R; 260/553 A
[51] Int. Cl.² ........................................ C07C 155/02
[58] Field of Search ......... 260/553 A, 553 R, 453 R

[56] References Cited
UNITED STATES PATENTS

| | | | |
|---|---|---|---|
| 3,344,153 | 9/1967 | Kuhle et al. | 260/453 RW |
| 3,652,630 | 3/1972 | Brown | 71/66 X |
| 3,711,530 | 1/1973 | Kobzina et al. | 71/98 X |
| 3,755,437 | 8/1973 | Brown | 71/98 X |
| 3,853,966 | 12/1974 | Brown | 260/553 A X |
| 3,857,883 | 12/1974 | Cleveland | 260/553 R X |

OTHER PUBLICATIONS

Mono–Olefins, Chemistry and Technology, Asinger, ed., pp. 714 and 715 (1969).

*Primary Examiner*—Robert V. Hines
*Assistant Examiner*—Thomas A. Waltz
*Attorney, Agent, or Firm*—G. F. Magdeburger; Dix A. Newell; Raymond Owyang

[57] ABSTRACT

Herbicidal 2-chlorocycloalkylthio urea compounds are produced by the 1,2-addition of an N-chlorothio urea to cycloalkenes. The N-chlorothio urea reactant is produced by the reaction of a urea and sulfur dichloride.

11 Claims, No Drawings

PREPARATION OF 2-CHLOROCYCLOALKYLTHIO UREA COMPOUNDS

RELATED APPLICATION

This application is a continuation-in-part of application Serial No. 250,895, filed May 8, 1972, now U.S. Pat. No. 3,857,883, the disclosure of which is incorporated herein by reference.

BACKGROUND OF THE INVENTION

1. Field of the Invention

This invention relates to a new process for the preparation of herbicidal 2-chlorocycloalkylthio urea compounds. 2. Description of the Prior Art Herbicidal 2-chlorocycloalkylthio urea compounds are disclosed in U.S. Pat. No. 3,711,530, issued Jan. 16, 1973 to John W. Kobzina et al.

E. Kuhle, Synthesis, 56 (1971), discloses the addition of aryl and aliphatic sulfenyl halides to olefins.

SUMMARY OF THE INVENTION

It has now been found that herbicidal 2-chlorocycloalkylthio ureas can be produced by the 1,2-addition of an N-chlorothio urea to a cycloalkene. By way of illustration, the addition of N-chlorothio urea to cyclohexene is depicted by the following reaction (1):

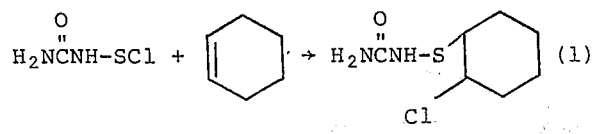

DESCRIPTION OF THE INVENTION

The N-Chlorothio Urea Reactant

The N-chlorothio urea reactant suitably employed in the process of the invention is represented by the formula (I):

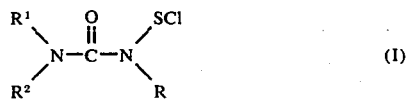

wherein R, $R^1$ and $R^2$ are hydrogen, alkyl of 1 to 6 carbon atoms, cycloalkyl of 3 to 10 carbon atoms, preferably 5 to 6 carbon atoms, carbocyclic mononuclear or binuclear aryl of 6 to 12 carbon atoms substituted with up to 4 (0 to 4), preferably up to 2 (0 to 2) fluoro, chloro, bromo, trifluoromethyl, trichloromethyl, nitro or alkoxy of 1 to 4 carbon atoms.

Representative alkyl groups which R, $R^1$ and $R^2$ may represent include methyl, ethyl, n-propyl, isopropyl, n-butyl, t-butyl, n-pentyl and n-hexyl. The preferred alkyl group is methyl.

Representative cycloalkyl groups which R, $R^1$ and $R^2$ may represent include monocyclic groups such as cyclopropyl, cyclopentyl, cyclohexyl, 2-methylcyclohexyl, 4-methylcyclohexyl, cycloheptyl and cyclooctyl; and bicyclic groups such as bicyclo[3.2.0]heptyl, bicyclo[2.2.1]heptyl, bicyclo[3.3.0]-octyl, bicyclo[4.2.0]octyl, bicyclo[3.3.0]octyl, and bicyclo[3.2.1]octyl. Cycloalkyl groups preferably are monocyclic groups having 5 to 6 carbon atoms.

Representative alkoxy groups which R, $R^1$ and $R^2$ may represent include methoxy, ethoxy, propoxy, butoxy, etc.

Representative hydrocarbyl aryl groups which R, $R^1$ and $R^2$ may represent include phenyl; naphthyl; alkylphenyl of 7 to 10 carbon atoms such as 2-methylphenyl, 3-methylphenyl, 4-ethylphenyl, 2,4-dimethylphenyl, 3,4-dimethylphenyl, 3-secbutylphenyl; and phenylalkyl of 7 to 10 carbon atoms such as benzyl, 3-phenylpropyl and 4-phenylbutyl.

Representative substituted aryl groups which R, $R^1$ and $R^2$ may represent include halo-substituted phenyl, alkylphenyl or phenylalkyl groups such as 2-fluorophenyl, 4-fluorophenyl, 2-chlorophenyl, 3-bromophenyl, 3,4-dichlorophenyl, 4-trifluoromethylphenyl, 3-chloro-4-bromophenyl, 2-chloro-4-methylphenyl, 2-fluoro-4-methylphenyl, 4-chlorobenzyl, 4-fluorobenzyl, 2-(2-fluorophenyl)ethyl; alkoxy-substituted phenyl, alkylphenyl or phenylalkyl such as 4-methoxyphenyl, 4-ethoxyphenyl, 4-methoxy-2-methylphenyl, 4-methoxybenzyl; nitrosubstituted phenyl, alkylphenyl or phenylalkyl groups such as 2-nitrophenyl, 4-nitrophenyl and 4-nitrobenzyl; and aryl groups substituted with different substituents such as 2-methoxy-4-chlorophenyl and 2-chloro-4-nitrophenyl. Substituted aryl groups preferably have 1 to 2 substituents. Preferred aryl groups are halo-substituted phenyls, especially those having 1 to 2 fluorine or chlorine substituents.

Preferably R is alkyl of 1 to 3 carbon atoms, especially methyl.

Preferably $R^1$ is phenyl or phenyl substituted with 1 to 2 fluorine, chlorine, trifluoromethyl groups, nitro groups, alkyl of 1 to 3 carbon atoms, or alkyoxy of 1 to 2 carbon atoms.

Preferably $R^2$ is hydrogen or alkyl of 1 to 3 carbon atoms. The most preferred $R^2$ group is hydrogen.

A preferred class of N-chlorothio urea reactants is that wherein at least one R, $R^1$ or $R^2$ group is hydrogen.

The N-chlorothio urea reactant (I) is prepared in accordance with the following reaction (2):

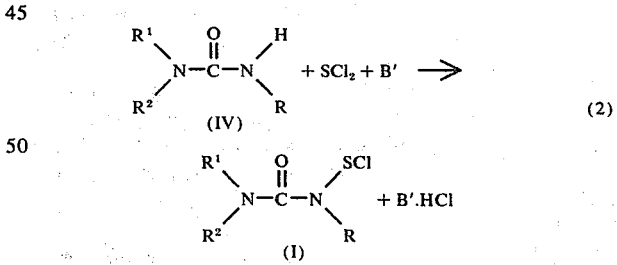

wherein R, $R^1$ and $R^2$ have the same significance as previously defined and B' is an acid acceptor.

The acid acceptor is an inorganic base, e.g., alkali metal hydroxide, bicarbonate or carbonate, or an organic nitrogen base having no N-H groups, such as a pyridine compound or a trialkylamine. Suitable pyridine compounds are pyridine and pyridine compounds of 6 to 10 carbon atoms and of 1 to 2 alkyl groups such as 2-methyl-pyridine, 2-ethylpyridine, 3-methylpyridine, 3,5-dimethylpyridine, and 2-butylpyridine. Suitable trialkylamines are those wherein the alkyl group contains individually 1 to 4 carbon atoms, such as trimethylamine, triethylamine, tripropylamine and tributylamine. The preferred acid acceptors are pyridine compounds, especially pyridine.

Generally, commercially available sulfur dichloride of reasonable purity, e.g., greater than 90–98% purity, is suitable employed. The sulfur dichloride may contain small amounts of an inhibitor such as tributylphosphate or triethylphosphate.

The sulfur dichloride and the urea (IV) are employed in substantially equimolar amounts, e.g., the molar ratio of sulfur dichloride to the urea compound generally varies from about 1.5:1 to 1:1.5, although molar ratios of sulfur dichloride to the urea compound of 1.4:1 to 1.1:1 are preferred. The molar ratios of acid acceptor to sulfur dichloride are also substantially equimolar, e.g., the molar ratio of acid acceptor to sulfur dichloride varies from about 1.5:1 to 1:1.5, although molar ratios of acid acceptor to sulfur dichloride of 1:1 to 1:1.2 are preferred.

In general, reaction (2) is accomplished by reacting the urea compound (IV) and the sulfur dichloride in the presence of the acid acceptor compound in the liquid phase in an inert diluent. The reaction is suitably conducted by adding the sulfur dichloride to a mixture of the urea and the acid acceptor in an inert diluent. Alternatively, the reaction is conducted by adding a mixture of the urea and acid acceptor to a solution of the sulfur dichloride in an inert diluent. However, the preferred method for conducting the reaction comprises reacting the urea and sulfur dichloride in the presence of a limited amount of free uncomplexed acid acceptor. This is suitably accomplished by the addition of the acid acceptor to a substantially equimolar mixture of the urea and the sulfur dichloride so that the mols of free acid acceptor to the total mols of urea reactant and N-chlorothio urea product is less than 0.2:1, preferably less than 0.1:1, and more preferably less than 0.05:1. In other words, during the course of the reaction between the sulfur dichloride and the urea reactant, there should be at least 5 mols of the urea reactant and the N-chlorothio urea product per mol of acid acceptor which is not complexed with hydrochloric acid. Provided that the reaction is conducted with the restricted amount of acid acceptor indicated above, the contacting of the acid acceptor with the mixture of the urea and the sulfur dichloride can be conducted by a variety of procedures. In one modification, the acid acceptor is added in increments, e.g., dropwise, in an inert diluent, if desired, to a mixture of the urea and sulfur dichloride in an inert diluent. In another modification, the acid acceptor is added continuously to a mixture of the urea and sulfur dichloride in an inert diluent.

Suitable inert diluents for reaction (2) include alkanes of 5 to 10 carbon atoms, such as hexane, isooctane and decane; aromatic compounds such as benzene and chlorobenzene, oxygenated hydrocarbons such as acyclic alkyl ethers, e.g., dimethoxyethane and dibutyl ether; and cycloalkyl ethers, e.g., dioxane, tetrahydrofuran and tetrahydropyran. Other suitable diluents include nitriles such as acetonitrile and propionitrile, dialkylamides such as dimethylformamide and dialkylsulfoxides such as dimethylsulfoxide. Preferred diluents are chlorinated hydrocarbons of 1 to 2 carbon atoms, such as methylene dichloride, chloroform, carbon tetrachloride and ethylene dichloride. Generally, the amount of diluent employed ranges from 1 to 50 mols per mol of N-chlorothio urea reactant.

Reaction (2) is suitably conducted at a temperature between −20°C. and the boiling point of the diluent, although temperatures between 0°C. and 50°C. are preferred. The reaction is conducted at or above atmospheric pressure.

The N-chlorothio urea is suitablly isolated from the reaction mixture by conventional procedures such as extraction, distillation, chromatography, etc. Alternatively, a solution of the N-chlorothio urea in the reaction diluent, preferably after removal of the acid acceptor hydrochloride salt produced in the reaction, is reacted with the cycloalkene (II) according to reaction (3) to produce the urea product (III) of the invention.

Alternative methods for producing the N-chlorothio urea reactant (I) are disclosed by E. Kühle, Synthesis, 11 573 (1970), and German Pat. No. 2,045,440 of Farbenfabriken Bayer AG, published March 23, 1973.

The Cycloalkene Reactant

The cycloalkene reactant is a monocyclic olefin of 4 to 10 carbon atoms. Representative cycloalkene reactants are therefore cyclobutene, cyclopentene, 1-methylcyclopentene, cyclohexene, 1-methylcyclohexene, 4-methylcyclohexene, cycloheptene, cyclooctene, cyclodecene, etc.

A preferred class of cycloalkene reactants is represented by the formula

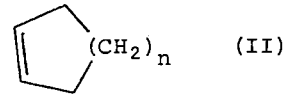

wherein n is 1 to 5, preferably 2 to 4.

2-chlorocycloalkylthio Urea Products

In terms of the N-chlorothio urea reactant (I) and the cycloalkene reactant (II), the formation of the urea products of the process of the invention may be depicted by the following reaction (3):

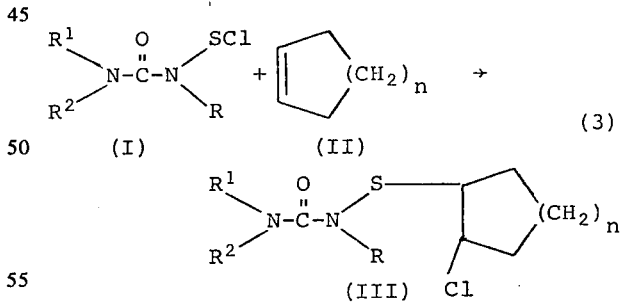

wherein R, $R^1$, $R^2$ and n are as defined above.

The addition of N-chlorothio urea reactant (I) to the cycloalkene (II) according to reaction (3) is conducted in the liquid phase in an inert diluent, preferably the same inert diluents employed in the preparation of the N-chlorothio urea reactant (I). The preferred diluents are chlorinated hydrocarbons of 1 to 2 carbon atoms, such as methylene dichloride, chloroform, carbon tetrachloride and ethylene dichloride. Generally, the amount of diluent employed ranges from 1 to 50 mols per mol of N-chlorothio urea reactant.

The N-chlorothio urea reactant (I) and the cycloalkene (II) are generally employed in substantially equimolar amounts, e.g., the molar ratio of the urea (I) to the cycloalkene (II) generally varies from 1.5:1 to 1:1.5. However, an excess of the cycloalkene (II) is suitably employed. For example, in some modifications of the process of the present invention, it is desirable to employ excess cycloalkene as the reaction diluent. Accordingly, molar ratios of N-chlorothio urea (I) to cycloalkene (II) of from 1.5:1 to 1:10 are satisfactorily employed.

Reaction (3) is suitably conducted at a temperature between −20°C. and the boiling point of the diluent, although temperatures between 0°C. and 50°C. are preferred. The reaction is conducted at or above atmospheric pressure.

The 2-chlorocycloalkylthio urea product (III) is recovered by conventional procedures such as extraction, crystallization, chromatography, etc.

Representative ureas of formula (III) are:

N-(2-chlorocyclopentylthio)-N-methyl-N'-(3,4-dichlorophenyl) urea,

N-(2-chlorocyclohexylthio)-N-methyl-N'-(2-trifluoromethylphenyl) urea,

N-(2-chlorocycloheptylthio)-N'-methyl-N,N'-dimethoxy urea,

N-(2-chlorocyclohexylthio)-N-butyl-N'-(4-nitrobenzyl) urea,

N-(2-chlorocyclohexylthio)-N-methyl-N'-(2-nitrophenyl) urea,

N-(2-chlorocyclooctylthio)-N-(3-trifluoromethylphenyl)-N',N'-dimethyl urea,

N-(2-chlorocyclopentylthio)-N-(3,4-dichlorophenyl-N'-methoxy-N'-methyl urea,

N-(2-chlorocyclodecylthio)-N-(3-chloro-4-bromophenyl)-N'-methoxy-N'-methyl urea, N-(2-chlorocyclohexylthio)-N-(3,4-dichlorophenyl)-N'-N'-dimethyl urea, N-(2-chlorocyclohexylthio)-N-(4-chlorophenyl)-N'-N'-dimethyl urea, N-(2-chlorocyclohexylthio)-N-(hexahydro-4,7-methanoinden-5-yl)-N',N'-dimethyl urea, N-(2-chlorocyclopentylthio)-N-(2-fluorophenyl)-N'-phenyl-N'-methyl urea, N-(2-chloro-3-methylcyclohexylthio)-N-(2-fluorophenyl)-N'-benzyl-N'-methyl urea, N-(2-chlorocyclohexylthio)-N-(2-fluorophenyl)-N'-methyl-N'-methyl-N'-propyl urea, N-(2chlorocyclohexylthio)-N-(2-fluoro-4-methylphenyl)-N'-(2-fluorophenyl)-N'-methyl urea, N-(2-chlorocyclohexylthio)-N-methyl-N'-(4-methoxyphenyl)-N'-methyl urea, and N-(2-chlorocyclohexylthio)-N-(3,4-dichlorophenyl)-N',N'-dimethyl urea.

EXAMPLES

The preparation of the ureas of the invention is illustrated by the following examples.

Example 1 — Preparation of N-chlorothio-N-methyl-N'-(2-fluorophenyl) urea

A 5.7-g (0.055 mol) sample of sulfur dichloride was added dropwise to a mixture of 8.4 g (0.05 mol) N-methyl-N'-2-fluorophenyl urea and 4.7 g (0.06 mol) pyridine in 50 ml methylene chloride cooled in an ice bath. After the completion of the addition, the pyridine hydrochloride formed during the reaction was filtered. Hexane was added to the filtrate to precipitate additional pyridine hydrochloride, which was removed by filtration. Evaporation of the resulting filtrate gave a clear red oil. The nuclear magnetic resonance (NMR) spectrum of the oil showed an N-methyl singlet at 3.5 ppm (relative to tetramethylsilane). Elemental analysis showed: %S, calc. 13.6, found 13.6; %Cl, calc. 15.1, found 15.4.

Example 2 — Preparation of N-chlorothio-N-(3,4-dichlorophenyl)-N',N'-dimethyl urea A 5.7-g (0.055 mol) sample of sulfur dichloride was added dropwise to a mixture of 11.7 g (0.05 mol) of N-(3,4-dichlorophenyl)-N',N'-dimethyl urea and 4.7 g (0.06 mol) pyridine in 50 ml methylene chloride cooled in an ice bath. After the completion of the addition, the pyridine hydrochloride was filtered. Hexane was added to precipitate additional pyridine hydrochloride, which was removed by filtration. Evaporation of the resulting filtrate gave the product as a clear yellow oil. The NMR spectrum showed an N',N'-dimethyl singlet at 3.0 ppm (relative to tetramethylsilane). Elemental analysis showed:

%S, calc. 10.7, found 10.7; %Cl, calc. 35.6, found 35.4; %C, calc. 36.1, found 36.4; %H, calc. 3.0, found 3.2; %N, calc. 9.3, found 8.7.

Example 3 — Preparation of N-chlorothio-N-methyl-N'-3,4-dichlorophenyl urea

A 9.48-g (0.12 mol) sample of pyridine was added dropwise to a slurry of 21.9 (0.1 mol) N-methyl-N'-(3,4-dichlorophenyl) urea and 11.3 g (0.11 mol) sulfur dichloride in 100 ml methylene dichloride at 25°–30°C. After the completion of the addition, pyridine hydrochloride was filtered from the reaction mixture. The NMR spectrum of the reaction mixture showed a singlet at 3.5 ppm (relative to tetramethylsilane) for the N-methyl group of the N-chlorothio-N-methyl-N'-3,4-dichlorophenyl urea product.

Example 4 — Preparation of N-chlorothio-N,N'-dimethyl urea

Pyridine (9.48 g, 0.12 mol) was added dropwise to a solution of 8.8 g (0.1 mol) N,N'-dimethyl urea and 11.3 g (0.11 mol) sulfur dichloride at 25°–30°C. Pyridine hydrochloride was then filtered from the reaction mixture to give a solution of the N-chlorothio urea product in methylene chloride. The NMR spectrum of the product showed a singlet at 3.5 ppm for the N-methyl group and a doublet at 2.95 ppm for the N'-methyl group.

Example 5 — Preparation of N-methyl-N-(2-chlorocyclohexylthio)-N'-(2-fluorophenyl urea A 569-g (7.2 mol) sample of pyridine was added at 25°–30°C. over a period of 18 minutes to a mixture of 1008 g (6 mols) of N-methyl-N'-(2-fluorophenyl) urea and 680 g (6.6 mols) sulfur dichloride in 6 liters methylene dichloride cooled with a dry ice/acetone bath. After the addition was completed, the pyridine hydrochloride salt was filtered. A 443-g (5.4 mol) sample of cyclohexene was then added to the resulting filtrate cooled to 0°C. with a dry ice/acetone bath. After 15 minutes of stirring, the resulting reaction mixture was washed with water, washed with sodium bicarbonate solution, dried over magnesium sulfate and evaporated under reduced pressure to give 1.7 kg of urea product as a yellow oil. U.S. Pat. No. 3,711,530 discloses that the urea product of this example has herbicidal activity.

Example 6 — Preparation of N-methyl-N-(2-chlorocyclooctylthio)-N'-(3,4-dichlorophenyl) urea An 11.0-g (0.1 mol) sample of cyclooctane was added dropwise at 0°C. to a solution of 0.1 mol N-chlorothio-N-methyl-N'-(3,4-dichlorophenyl) urea, prepared by a procedure similar to that of Example 3, in methylene dichloride. After the addition was completed, the reaction mixture was washed successively with water, aqueous sodium bicarbonate solution and water, dried over magnesium sulfate and evaporated to give a solid residue. The solid was recrystallized from isopropyl alcohol and washed with hexane to give 15 g of product, m.p. 90°–91°C. Elemental analysis for $C_{16}H_{21}Cl_3N_2OS$ showed: %S, calc. 8.1, found 8.2; %Cl, calc. 26.9, found 27.4.

Using the test procedure of US. Pat. No. 3,711,530, the product was found to be active for the control of wild oats, watergrass, crabgrass, pigweed, lambsquarter and mustard.

Example 7 — Preparation of N-methyl-N-(2-chlorocycloheptylthio)-N'-(3,4-dichlorophenyl) urea Example 7 Preparation of N-methyl-N-(2-chlorocyclo-heptylthio)-N'-(3,4-dichlorophenyl) urea The product, a white solid melting at 71°–72°C., was prepared from N-chlorothio-N-methyl-N'-(3,4-dichlorophenyl) urea and cycloheptene by a procedure similar to that of Example 6. Elemental analysis for $C_{15}H_{19}Cl_3N_2OS$ showed: %S, calc. 8.4, found 8.7; %Cl, calc. 27.9, found 27.7.

Using the test procedure of U.S. Pat. No. 3,711,530, the product was found to be active for the control of wild oats, watergrass, crabgrass, pigweed, lambsquarter and mustard.

What is claimed is:

1. In the process of preparing urea compounds which comprises:
   1. reacting substantially equimolar amounts of a urea reactant of the formula

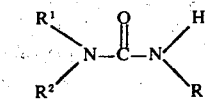

wherein R, $R^1$ and $R^2$ are hydrogen, alkyl of 1 to 6 carbon atoms, cycloalkyl of 3 to 10 carbon atoms, carbocyclic aryl of 6 to 12 carbon atoms substituted with up to a 4 fluoro, chloro, bromo, trifluoromethyl, trichloromethyl, nitro or alkoxy of 1 to 4 carbon atoms, and sulfur dichloride in the presence of an acid acceptor, and
   2. adding the resulting N-chlorothio urea product to a cycloalkene of 4 to 10 carbon atoms in the liquid phase in an inert diluent,
   the improvement which comprises maintaining during step (1) the mols of uncomplexed acceptor to the total mols of urea reactant and N-chlorothio urea product at a ratio of less than 0.2:1 by the controlled addition of the acceptor to a mixture of the urea reactant and sulfur dichloride.

2. The process of claim 1 wherein the ratio of unreacted acceptor to the total mols of urea reactant and N-chlorothio urea product is less than 0.1:1.

3. The process of claim 1 wherein the acid acceptor is a nitrogen organic base having no free N-H group.

4. The process of claim 3 wherein the organic base acceptor is pyridine.

5. The process of claim 1 wherein the ratio of unreacted acceptor to the total mols of urea reactant and N-chlorothio urea product is less than 0.05:1.

6. The process of claim 1 wherein R is alkyl of 1 to 2 carbon atoms.

7. The process of claim 6 wherein $R^2$ is hydrogen and $R^1$ is phenyl or phenyl substituted with 1 to 2 fluoro, chloro, trifluoromethyl, nitro, alkyl of 1 to 3 carbon atoms, or alkoxy of 1 to 2 carbon atoms.

8. The process of claim 7 wherein $R^1$ is phenyl substituted with 1 to 2 fluoro or chloro.

9. The process of claim 8 wherein R is methyl, $R^1$ is 2-fluorophenyl and $R^2$ is hydrogen.

10. The process of claim 8 wherein R is methyl, $R^1$ is 3,4-dichlorophenyl and $R^2$ is hydrogen.

11. The process of claim 1 wherein at least one R, $R^1$ or $R^2$ is hydrogen.

* * * * *